United States Patent [19]

Shibata et al.

[11] Patent Number: 4,814,436

[45] Date of Patent: Mar. 21, 1989

[54] DERIVATIVE OF α, α-TREHALOSE AND A PROCESS FOR PREPARING THE SAME

[75] Inventors: Akihiro Shibata, Narashino; Hideaki Matsuda, Abiko; Hidehiko Kohya, Sendai; Tatsuhiko Katori, Tone, all of Japan

[73] Assignee: SS Pharmaceutical Co., Ltd., Tokyo, Japan

[21] Appl. No.: 938,883

[22] Filed: Dec. 8, 1986

[30] Foreign Application Priority Data

Dec. 16, 1985 [JP] Japan ................................ 60-282676

[51] Int. Cl.[4] .................... C07H 13/02; A61K 31/715
[52] U.S. Cl. .................................. 536/17.1; 536/117; 536/119
[58] Field of Search ....................... 536/17.1, 117, 119

[56] References Cited

U.S. PATENT DOCUMENTS

| | | | |
|---|---|---|---|
| 4,612,304 | 9/1986 | Fukushi | 536/119 |
| 4,684,719 | 8/1987 | Nishikawa et al. | 536/119 |
| 4,720,456 | 1/1988 | Wagner et al. | 536/16.8 |

*Primary Examiner*—Ronald W. Griffin
*Attorney, Agent, or Firm*—Oblon, Fisher, Spivak, McClelland & Maier

[57] ABSTRACT

Derivatives of α,α-trehalose-6,6'-fatty acid diester having phosphoric ester groups in the molecule which are useful as a carcinostatic agent. One of the derivatives may be prepared by reacting diphenylphosphoryl chloridate with a derivative of 2,3,2',3'-tetra-O-benzyl-α,α-trehalose-6,6'-fatty acid diester. Another derivative may be obtained by substituting benzyl groups at 2,3,2',3' positions of trehalose with hydrogen atoms.

8 Claims, No Drawings

DERIVATIVE OF α,α-TREHALOSE AND A PROCESS FOR PREPARING THE SAME

BACKGROUND OF THE INVENTION

1. Field of the Invention

This invention relates to a derivative of α,α-trehalose useful as a medicine and, more particularly, to a derivative of α,α-trehalose-6,6'-fatty acid diester having phosphoric ester groups in the molecule thereof which is useful as a carcinostatic agent and to a process for preparing the same.

2. Description of the Prior Art

It is well known that α,α-trehalose fatty acid derivatives esterifed with various fatty acids such as mycolic acid possess carcinostatic activity.

These α,α-trehalose derivatives, however, are not yet satisfactory in the carcinostatic activity and water-solubility; thus the development of a novel compound having an improved properties has been desired.

SUMMARY OF THE INVENTION

The present inventors have synthesized various trehalose derivatives and investigated thier physiological activities in order to obtain a novel compound which is useful as a medicine. As a result, it was found that α,α-trehalose derivatives represented by the following formula (I):

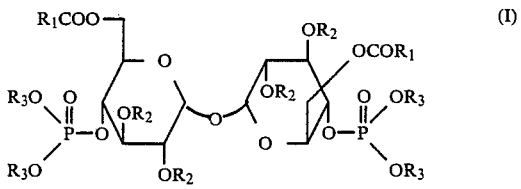

wherein $R_1$ represents an alkyl group having 1-29 carbon atoms, $R_2$ represents a hydrogen atom or a benzyl group and $R_3$ represents a hydrogen atom or a phenyl group had remarkable carcinostatic activity and was readily soluble in water. Such a finding has led to completion of this invention.

Accordingly, the object of this invention is to provide a novel derivative of α,α-trehalose represented by the above formula (I) and a process for preparing the same.

DETAILED DESCRIPTION OF THE INVENTION AND PREFERRED EMBODIMENTS

The α,α-trehalose derivatives according to this invention which are generally represented by the formula (I) are classified into two groups of compounds, each represented by the following formulae (Ia) and (Ib):

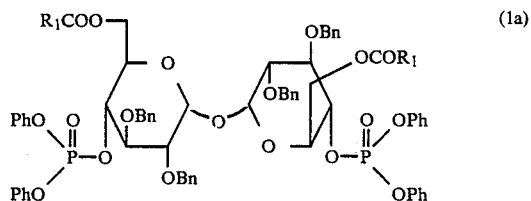

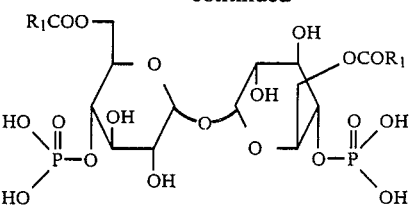

wherein Bn represents a benzyl group, Ph represents a phenyl group, and $R_1$ has the same meaning as defined above.

The compound of the formula (I) may be prepared, for example, according to the following processes.

[Process 1]

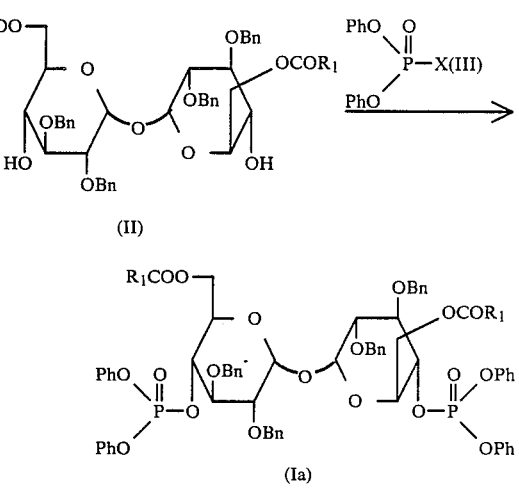

wherein $R_1$, Bn and Ph have the same meaning as defined above.

A phosphoric ester (III) is caused to react with a derivative of 2,3,2',3'-tetra-O-benzyl-α,α-trehalose-6,6'-fatty acid diester (II) to obtain a derivative of 2,3,2',3'-tetra-O-benzyl-4,4'-bis-O-(diphenylphosphono)-α,α-trehalose-6,6'-fatty acid diester (Ia).

The reaction is carried out using 2-5 moles of a phosphoric ester (III) per one mole of the compound (II) in the presence of a base and at a temperature of 0°-50° C. for 1-48 hours.

A base used for the reaction may be, for example, pyridine, picoline, lutidine, collidine, 4-dimethylaminopyridine, triethylamine, etc. A mixture of two or more of these bases may also be used. As a solvent for the reaction, chloroform, methylene chloride and the like may be preferably employed.

The compound (Ia) may be obtained in a purified form by distilling off the solvent from the reactant mixture under reduced pressure, dissolving the residue into a solvent such as hexane/ethyl acetate, removing the undissolved substance from the solute, and then purifying the solute, for instance, by means of silica gel column chromatography.

The raw material for the above reaction, i.e., a derivative of 2,3,2',3'-tetra-O-benzyl-α,α-trehlose-6,6'-fatty acid diester (II), is a known compound, and may be prepared via four steps from α,α-trehalose (Japanese Patent Application Laid Open No. 185599/1983).

[Process 2]

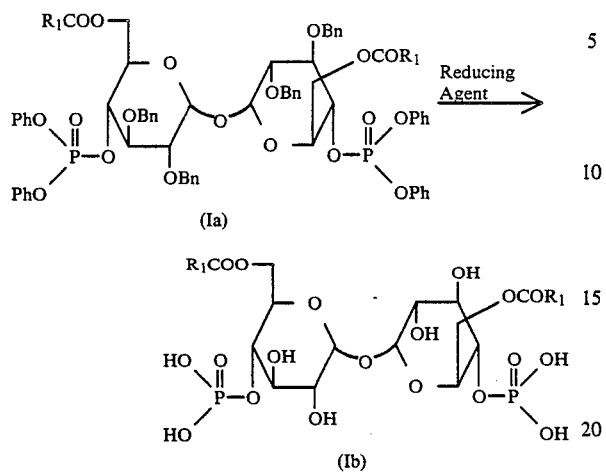

A derivative of 4,4'-di-O-phosphono-α,α-trehalose-6,6'-fatty acid diester (Ib) is prepared by catalytically reducing a derivative of 2,3,2',3'-tetra-O-benzyl-4,4'-bis-O-(diphenylphosphono)-α,α-trehalose-6,6'-fatty acid diester (Ia) in the presence of a reducing catalyst. The reaction is preferably proceeded in two steps. That is, the compound (Ia) is first catalytically reduced by hydrogen using reducing catalyst such as palladium black, palladium carbon and the like, in the amount of 0.01–1 part by weight per unit weight of the compound (Ia), at room temperature—50° C. and 1–5 hours. After filtering off the reducing catalyst, the material is again subjected to reduction by hydrogen using a reducing agent such as platinum black, in the amount of 0.01–1 part by weight per unit weight of the starting material (Ia), at room temperature—50° C. and for 1–50 hours. The solvent to be used for the reaction may be acetic acid, methanol, ethanol, isopropanol, and the like. The mixed solvent of two or more of these solvents may also be useful.

In the above reaction, the compound (Ia) can be quantitatively converted into the aimed compound (Ib). Thus, after completion of the reaction, the pure compound (Ib) may be obtained by filtering off the reducing catalyst and distilling off the solvent from the filtrate.

Carcinostatic activity of the inventive compound (Ib) was investigated. The procedure and the test result otained were as follows.

Therapeuic Effect of the Inventive Compound against Meth-A Tumor:

Bal β/c mice (age: 7 weeks; male) were cutaneously transplanted with $1 \times 10^6$ Meth-A tumor cells (Primary Transplantation). The same mice which had previously sustained the Primary Transplantation and had been completely cured by administration of the inventive compound was again transplanted with $5 \times 10^5$ Meth-A tumor cells (Secondary Transplantation). On the 3rd day of the tumor transplantation each animal was injected into its tumor with 3 mg of the inventive compound dissolved in phosphate buffer of PH 7.2. Observation was conducted for 21 days after transplantation. The effect of the compound against the tumor was indicated by (The Numbers of Completely Cured Animals versus the Numbers of Tested Animals). The result is shown in Table 1 below:

TABLE 1

| Tested Compound No.* | Completely Cured Animals/ Tested Animals | |
|---|---|---|
| | Primary Transplantation | Secondary Transplantation |
| Controls | 0/8 | — |
| 15 | 5/7 | 2/5 |
| 16 | 5/7 | 1/5 |
| 17 | 6/7 | 3/6 |

*"Compound No." designates the inventive compound prepared according to the process of this invention and listed in Table 2 hereinafter.

As described above, the inventive product possesses carcinostatic activity and thus is useful as carcinostatic agent. Since the product also has a good solubility to water, it may be made into an aqueous injection by dissolving it or the salt thereof, for example, the sodium salt thereof in water.

The invention is hereinbelow descrived by means of examples.

EXAMPLE 1

Synthesis of 2,3,2',3'-tetra-O-benzyl-6,6'-di-O-decanoyl-4,4'-bis-O-(diphenylphosphono)-α,α-trehalose (Compound No. 5):

5.06 g of 2,3,2',3'-tetra-O-benzyl-6,6'-di-O-decanoyl-α,α-trehalose (II) was dissolved into 100 ml of methylene chloride and added with 1.47 g of 4-dimethylaminopyridine and 0.95 g of pyridine, to which a solution of 5.38 g of diphenylphosphoryl chloridate in 20 ml of methylene chloride was added dropwise over 20 minutes and under stirring. After completing the addition of the solution, the stirring was continued for 17 hours at room temperature. Then, the solvent was distilled off and the residue was added with 20 ml of a mixed solvent of hexane/ethyl acetate (20:1). The substance insoluble to the solvent was removed, and soluble substance was collected by distilling off the solvent. The latter substance was purified by means of column chromatography using hexane/ethyl acetate as an eluent to obtain 6.51 g of the aimed compound of colorless syrup (yield: 88.2%).

EXAMPLE 2

Synthesis of 6,6'-di-O-decanoyl-4,4'-di-O-phosphono-α,α-trehalose (Compound No. 15):

2.22 g of 2,3,2',3'-tetra-O-benzyl-6,6'-di-O-decanoyl-4,4'-bis-O-(diphenylphosphono)-α,α-trehalose (Compound No. 5) was dissolved into 50 ml of isopropanol and 50 ml of acetic acid and added with 0.5 g of palladium black. The mixture was stirred under hydrogen atmosphere for 3 hours. The palladium black was filtered off and 0.5 g of platinum black was added to complete the reaction under hydrogen atmosphere while stirring the mixture for 17.5 hours. The reactant mixture was filtered and the solvent was distilled off from the filtrate to obtain 1.10 g of the aimed compound of colorless amorphous (yield: 90.5%).

EXAMPLE 3

The compounds listed in Table 2, other than Compounds No. 5 and 15, were prepared in the similar manner as Examples 1 and 2.

TABLE 2

Optical Rotation

TABLE 2-continued

| Comp'd No. | In Formula (I) R₁ | R₂ | R₃ | Property (Melting Point) | $[\alpha]_D^{27}$ °C. (C = 1.00, CHCl₃) | IR cm⁻¹ NaCl-film | ¹H—NMR ppm (CDCl₃, TMS, 60 MHz) |
|---|---|---|---|---|---|---|---|
| 1 | CH₃ | CH₂Ph | Ph | Colorless Syrup | +98.9° | 3040, 2950, 1738, 1590, 1487, 1290 | 6.8–7.4(40H, m), 5.10(2H, d, J=3.6), 4.89(4H, s), 4.63(4H, s), 3.7–4.5(10H, m), 3.60(2H, d, d, J=9.2, 3.6), 1.92(6H, s) |
| 2 | n-C₃H₇ | " | " | Colorless, needle-like crystal (mp. 95–96° C.) | +95.4° | 2960, 2880, 1730, 1588, 1490, 1287 | 6.8–7.4(40H, m), 5.04(2H, d, J=3.6), 4.83(4H, s), 4.58(4H, s), 3.8–4.5(10H, m), 3.56(2H, d, d, J=9.0, 3.6), 2.16(4H, t, J=6.8), 1.51(4H, t, q, J=6.8, 6.8), 0.82(6H, t, J=6.8) |
| 3 | n-C₅H₁₁ | " | " | Colorless, needle-like crystal (mp. 91–92° C.) | +91.5° | 2960, 2870, 1730, 1590, 1488, 1290 | 6.8–7.4(40H, m), 5.06(2H, d, J=3.6), 4.83(4H, s), 4.59(4H, s), 3.8–4.5(10H, m), 3.56(2H, d, d, J=9.0, 3.6), 2.17(4H, t, J=6.8), 1.0–1.8(12H, m), 0.82(6H, t-like) |
| 4 | n-C₇H₁₅ | " | " | Colorless Syrup | +83.7° | 2935, 2855, 1736, 1590, 1492, 1294 | 6.8–7.4(40H, m), 5.07(2H, d, J=3.6), 4.84(4H, s), 4.60(4H, s), 3.8–4.5(10H, m), 3.58(2H, d, d, J=9.0, 3.6), 2.18(4H, t, J=6.8), 1.20(20H, m), 0.85(6H, t-like) |
| 5 | n-C₉H₁₉ | " | " | Colorless Syrup | +82.4° | 2910, 2845, 1735, 1585, 1490, 1287 | 6.8–7.4(40H, m), 5.06(2H, d, J=3.6), 4.84(4H, s), 4.59(4H, s), 3.8–4.5(10H, m), 3.57(2H, d, d, J=9.0, 3.6), 2.16(4H, t, J=7.0), 1.22(28H, m), 0.86(6H, t-like) |
| 6 | n-C₁₁H₂₃ | " | " | Colorless Syrup | +80.6° | 2925, 2855, 1737, 1590, 1492, 1292 | 6.8–7.4(40H, m), 5.08(2H, d, J=3.6), 4.85(4H, s), 4.60(4H, s), 3.7–4.5(10H, m), 3.58(2H, d, d, J=9.0, 3.6), 2.17(4H, t, J=7.0), 1.23(36H, m), 0.87(6H, t-like) |
| 7 | n-C₁₃H₂₇ | " | " | Colorless Syrup | +77.2° | 2940, 2860, 1737, 1592, 1493, 1293 | 6.8–7.4(40H, m), 5.08(2H, d, J=3.6), 4.86(4H, s), 4.62(4H, s), 3.8–4.5(10H, m), 3.57(2H, d, d, J=9.0, 3.6), 2.18(4H, t, J=7.0), 1.25(44H, m), 0.87(6H, t-like) |
| 8 | n-C₁₅H₃₁ | " | " | Colorless Syrup | +75.8° | 2940, 2860, 1739, 1592, 1493, 1294 | 6.8–7.4(40H, m), 5.08(2H, d, J=3.6), 4.87(4H, s), 4.61(4H, s), 3.8–4.5(10H, m), 3.58(2H, d, d, J=9.0, 3.6), 2.18(4H, t, J=7.0), 1.25(52H, m), 0.87(6H, t-like) |
| 9 | n-C₁₇H₃₅ | " | " | Colorless Syrup | +71.4° | 2940, 2860, 1738, 1590, 1492, 1293 | 6.8–7.4(40H, m), 5.08(2H, d, J=3.6), 4.87(4H, s), 4.62(4H, s), 3.8–4.5(10H, m), 3.58(2H, d, d, J=9.0, 3.6), 2.18(4H, t, J=7.0), 1.25(60H, m), 0.87(6H, t-like) |
| 10 | n-C₂₁H₄₃ | " | " | Colorless Syrup | +64.6° | 2940, 2855, 1740, 1593, 1493, 1294 | 6.9–7.4(40H, m), 5.09(2H, d, J=3.6), 4.88(4H, s), 4.62(4H, s), 3.7–4.5(10H, m), 3.59(2H, d, d, J=9.0, 3.6), 2.19(4H, t, J=7.0), 1.25(76H, m), 0.88(6H, t-like) |

| Comp'd No. | In Formula (I) R₁ | R₂ | R₃ | Property | Optical Rotation $[\alpha]_D^{24}$ °C. (C = 1.00, MeOH) | IR cm⁻¹ KBr Tab | ¹H—NMR ppm (CD₃OD, TMS, 60 MHz*) |
|---|---|---|---|---|---|---|---|
| 11 | CH₃ | H | H | Colorless Amorphous | +126.1° | 3380, 2950, 1725, 1245, 1155, 1085 | 5.03(8H, s), 4.98(2H, d, J=3.6), 3.8–4.4(10H, m), 3.51(2H, d, d, J=9.0, 3.6), 2.03(6H, s) |
| 12 | n-C₃H₇ | " | " | Colorless Amorphous | +122.7° | 3400, 2965, 1725, 1718, 1200, 1085, 1025 | 5.05(8H, s), 4.91(2H, d, J=3.6), 3.7–4.5(10H, m), 3.43(2H, d, d, J=9.0, 3.6), 2.27(4H, t, J=7.0), 1.60(4H, t, q, J=7.0), 0.91(6H, t, J=7.0) |
| 13 | n-C₅H₁₁ | " | " | Colorless Amorphous | +116.9° | 3400, 2960, 1735, 1720, 1215, 1085, 1027 | 4.92(8H, s), 4.95(2H, d, J=3.6), 3.7–4.5(10H, m), 3.43(2H, d, d, J=9.0, 3.6), 2.28(4H, t, J=6.8), 1.0–1.8(12H, m), 0.89(6H, t, J=6.8) |
| 14 | n-C₇H₁₅ | " | " | Colorless Amorphous | +108.8° | 3400, 2940, 2855, 1733, 1722, 1226, 1153, 1082, 1030 | 5.02(8H, s), 4.98(2H, d, J=3.6), 3.8–4.5(10H, m), 3.48(2H, d, d, J=9.0, 3.6), 2.30(4H, t, J=7.0), 1.1–1.9(20H, m), 0.89(6H, t-like) |
| 15 | n-C₉H₁₉ | " | " | Colorless Amorphous | +100.2° | 3400, 2990, 1727, 1266, 1095, 1023 | 4.92(8H, s), 5.03(2H, d, J=3.5), 3.8–4.4(10H, m), 3.52(2H, d, d, J=9.0, 3.5), 2.35(4H, t, J=7.2), 1.30(28H, m), 0.90(6H, t-like) |
| 16 | n-C₁₁H₂₃ | " | " | Colorless Amorphous | +95.0° | 3380, 2930, 2853, 1735, 1723, 1153, 1028 | 5.08(8H, s), 4.96(2H, d, J=3.6), 3.7–4.5(10H, m), 3.48(2H, d, d, J=9.0, 3.6), 2.32(4H, t, J=7.0), 1.28(36H, m), 0.88(6H, t-like) |
| 17 | n-C₁₃H₂₇ | " | " | Colorless Amorphous | +89.2° | 3400, 2930, 2850, 1733, 1720, 1150, 1083, 1030 | 4.93(8H, s), 4.96(2H, d, J=3.6), 3.7–4.5(10H, m), 3.46(2H, d, d, J=9.0, 3.6), 2.30(4H, t, J=7.0), 1.24(44H, m), 0.88(6H, t-like) |
| 18 | n-C₁₅H₃₁ | " | " | Colorless Amorphous | +83.5° | 3400, 2930, 2855, 1733, 1210, 1153, 1085 | 4.98(8H, s), 4.96(2H, d, J=3.6), 3.7–4.5(10H, m), 3.48(2H, d, d, J=9.0, 3.6), 2.32(4H, t-like), 1.28(52H, m), 0.88(6H, t-like) |
| 19 | n-C₁₇H₃₅ | " | " | Colorless wax | +78.0° | 3380, 2930, 2855, 1735, 1720, 1257, 1152, 1083, | 4.83(8H, s), 4.96(2H, d, J=3.6), 3.7–4.5(10H, m), 3.47(2H, d, d, J=9.0, 3.6), 2.30(4H, t-like), 1.27(60H, m), 0.88(6H, t-like) |

TABLE 2-continued

| 20 | n-C$_{21}$H$_{43}$ | " | " | Colorless wax | +65.3° | 1025 3400, 2930, 2855, 1735, 1722, 1468, 1208, 1192 | 4.72(8H, s), 5.06(2H, d, J=3.7), 3.8–4.5(10H, m), 3.55(2H, d, d, J=9.0, 3.7), 2.35(4H, t, J=7.0), 1.29(76H, m), 0.90(6H, t-like) |
|---|---|---|---|---|---|---|---|

*90 MHz for Compounds 15 and 20

What is claimed is:

1. A derivative of α,α-trehalose represented by the following formula (I):

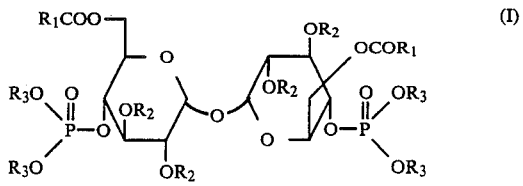

wherein $R_1$ represents an alkyl group having 1–29 carbon atoms, $R_2$ represents a hydrogen atom or a benzyl group and $R_3$ represents a hydrogen atom or a phenyl group.

2. A process for preparing a derivative of 2,3,2',3'-tetra-O-benzyl-4,4'-bis-O-(diphenylphosphono)-α,α-trehalose-6,6'-fatty acid diester represented by the formula (Ia):

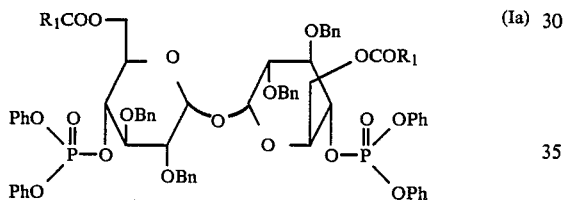

wherein
$R_1$ represents an alkyl group having 1–29 carbon atoms, Bn, represents a benzyl group and Ph represents a phenyl group, which comprises:
reacting a derivative of 2,3,2',3'-tetra-O-benzyl-α,α-trehalose-6,6'-fatty acid diester represented by formula (II):

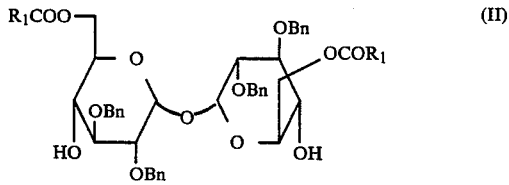

wherein $R_1$ and Bn each have the same meaning as defined above, with a phosphoric ester represented by formula (III):

wherein Ph has the same meaning as defined above and Y represents a halogen atom in a solvent in the presence of a base at a temperature of 0°–50° C.

3. The process according to claim 2, wherein said base is one or more bases selected from the group consisting of pyridine, picoline, lutidine, collidine, 4-methylaminopyridine, and triethylamine.

4. A process for preparing a derivative of 4,4'-di-O-phosphono-α,α-trehalose-6,6'-fatty acid diester represented by the formula (Ib):

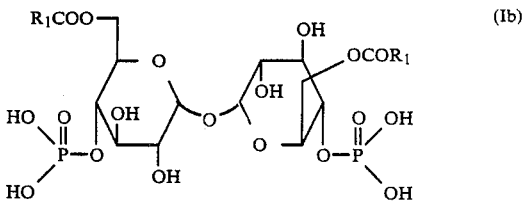

wherein
$R_1$ represents an alkyl group having 1–29 carbon atoms, which comprises:
reducing a derivative of 2,3,2',3'-tetra-O-benzyl-4,4'-bis-O-(diphenylphosphono)-α,α-trehalose-6,6'-fatty acid diester represented by the formula (Ia):

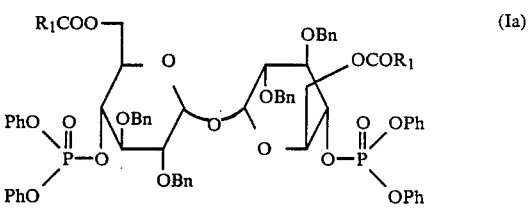

wherein
$R_1$ has the same meaning as defined above, Bn represents a benzyl group, and Ph represents a phenyl group with hydrogen in the presence of a reducing catalyst at a temperature in the range of from room temperature to 50° C.; and
further reducing the compound produced in the first step by hydrogen in the presence of a reducing catalyst at a temperature in the range of from room temperature to 50° C.

5. The process according to claim 4, wherein said catalyst used in said first reduction step is palladium black or palladium carbon and said catalyst used in said second reduction step is platinum black.

6. The process according to claim 4, wherein each of said catalysts in the first and second reducing steps is present in the reaction in the amount of 0.01–1 part by weight per 1 part by weight of said derivative of 2,3,2',3'-tetra-O-benzyl-4,4'-bis-O-(diphenylphosphono)-α,α-trehalose-6,6'-fatty acid diester.

7. The process according to claim 5, wherein each of said catalysts in the first and second reducing steps is present in the reaction in the amount of 0.01–1 part by weight per 1 part by weight of said derivative of 2,3,2',3'-tetra-O-benzyl-4,4'-bis-O-(diphenylphosphono)-α,α-trehalose-6,6'-fatty acid diester.

8. The process according to claim 4, wherein each of the reduction steps is conducted in a solvent of acetic acid, methanol, ethanol or isopropanol.

* * * * *